United States Patent [19]
Weissman

[11] Patent Number: 5,150,788
[45] Date of Patent: Sep. 29, 1992

[54] REAMER/WRENCH/POST KIT

[76] Inventor: Bernard Weissman, 225 E. 48th St., New York, N.Y. 10017

[21] Appl. No.: 678,785

[22] Filed: Apr. 1, 1991

[51] Int. Cl.⁵ .............................................. B65D 85/24
[52] U.S. Cl. .................................... 206/369; 206/370
[58] Field of Search ............... 206/368, 369, 370, 373, 206/374, 376, 378, 379, 533, 538, 539

[56] References Cited

U.S. PATENT DOCUMENTS

| | | | |
|---|---|---|---|
| 2,148,721 | 2/1939 | Avstreih | 206/369 |
| 2,780,349 | 2/1957 | Tornberg | 206/533 |
| 3,394,796 | 7/1968 | Jensen | 206/533 |
| 3,926,335 | 12/1975 | Dangles | 206/533 |
| 4,245,742 | 1/1981 | Rossmo | 206/533 |
| 4,288,006 | 9/1981 | Clover, Jr. | 206/538 |
| 4,449,630 | 5/1984 | Filhol | 206/369 |

FOREIGN PATENT DOCUMENTS

| | | | |
|---|---|---|---|
| 0557226 | 5/1958 | Canada | 206/533 |
| 2133091 | 1/1973 | Fed. Rep. of Germany | 206/538 |
| 0488075 | 12/1953 | Italy | 206/533 |
| 0606159 | 8/1948 | United Kingdom | 206/538 |

Primary Examiner—Jimmy G. Foster
Attorney, Agent, or Firm—Paul J. Sutton; Barry G. Magidoff

[57] ABSTRACT

This invention provides a compact and convenient dental tool container which is particularly useful for storing dental posts, post wrenches and reamers, and stops for reamers, plus a gauge, coordinating several of a dentist's requirements in a helpful way. A handheld circular tool holder has a number of peripheral compartments for the tools and a selector lid rotatable on the tool holder which selector lid has an opening to access the peripheral compartments. Optionally, a secondary compartment and access opening in the lid provide storage for the post wrenches. A novel breakaway tab locks the lid closed for distribution and marketing, and preferably engages in a unique gauge block for sizing the reamers; alternatively an indexing ratchet restricts rotation of the lid. The invention includes a kit comprising the container charged with the several tools described.

23 Claims, 11 Drawing Sheets

REAMER/WRENCH/POST KIT

BACKGROUND OF THE INVENTION

1. Field of the Invention

This invention lies generally in the field of dental equipment and more particularly relates to a new and improved dental tool container which has novel utility for dentists. More particularly, but not exclusively, the invention provides a dental tool container which is particularly useful for storing and measuring dental posts, post wrenches and reamers and stops, coordinating several of a dentist's requirements in a unique and helpful way.

2. The Prior Art

Dental tool containers are known which comprise an annular tool holder; a plurality of primary tool-storage compartments for dental posts which compartments are disposed around the tool holder; a selector lid rotatably mounted on the tool holder and covering the compartments; and a primary opening in the selector lid for accessing said primary compartments; whereby rotation of the selector lid can register said primary opening with each primary compartment in turn, providing access thereto.

Such tool holders have found widespread acceptance as a convenient means of storing and dispensing dental posts for dental drills.

It would be desirable to provide an improved tool holder which was also suitable for storing one or more dental post wrenches as well as the posts themselves. Even if a conventional post wrench could be fitted in a post compartment, which may not be the case, that post compartment is likely to be used inconsistently and the post wrenches are likely to be misplaced and hard to find.

It would also be desirable to provide a dental tool container having storage means for reamers. However, reamers are substantially longer than dental posts, requiring longer compartments, creating difficulty in devising a compact container that retains the simplicity and convenience of the prior art.

Gauges measuring diameter and length, have been available as separate items.

BRIEF SUMMARY OF THE INVENTION

It is one object of the present invention to provide an improved dental tool of the prior art type described above, which is particularly useful for storing and dispensing post wrenches as well as dental posts.

It is a further object of this invention to provide such a dental tool container which can store dental post wrenches in a unique, readily locatable manner.

Another object of this invention is to provide such a dental tool container which can store reamers, as well as dental posts, in a simple and compact construction.

A still further object of this invention is to provide such a dental tool container and associated tools in the form of a novel and useful kit, to make posts, reamers and wrenches conveniently available to a dentist.

Yet another object of this invention is to provide such a dental tool container which has means to lock the selector lid closed for marketing and distribution.

A further object is the means to include a stock of reamers of several different sizes in the container, and to provide a convenient means to measure or determine those sizes.

Accordingly, the present invention is based upon a dental tool container comprising:
- a cylindrical container having a circumferential outer wall and a bottom;
- a cylindrical inner wall, concentric with the outer wall;
- a plurality of substantially radially extending walls extending between the inner and outer walls to define a plurality of annular primary tool-storage compartments for dental posts, which compartments are disposed around the tool holder;
- a selector lid rotatably mounted on the tool holder and covering the compartments; except for
- a primary opening in the selector lid for accessing said primary compartments;

whereby rotation of the selector lid can register said primary opening with each primary compartment in turn, providing access thereto;

and wherein the tool container optionally further comprises in accordance with this invention:
- a secondary tool storage compartment for dental post wrenches, which secondary compartment is disposed, and extends, preferably radially within the cylindrical inner wall, and surrounded by said primary compartments; and
- a secondary opening in the selector lid for accessing said secondary compartment;

whereby rotation of the selector lid on the tool holder can bring the secondary opening therein into and out of registration with said secondary compartment to access it.

Preferably, one of said primary compartments is elongated to project radially inwards beyond the inner wall, so as to provide a relatively longer reamer compartment to accommodate reamers. The secondary compartment most preferably extends in line across the center to abut the reamer compartment.

In another preferred embodiment, a gauge is provided within a primary compartment, preferably opposite the elongated compartment; most preferably, the gauge also extends beyond the inner wall, towards the center and the elongated compartment; an opening is most preferably formed through the outer wall of the container and registering with a slot extending radially along the gauge.

In a preferred embodiment, the container includes a breakaway tab to lock the selector lid in a closed position for marketing and distribution.

As an alternative, a flexible pawl member extends from the lid and intersects with an indexing ratchet means on the exterior of the outer wall of the container.

With useful advantage, the invention also provides a gauge block in one of the primary compartments which block is adapted for measuring, both radially and longitudinally, tools to be stored in others of said compartments. This gauge block can be a close fit in a compartment to be stably supported therein. Preferably, the breakaway tab is adapted to engage the gauge block thereby to lock the selector lid against rotation and to hold the gauge block in its primary compartment. Alternatively, a removable plate extends across the lid opening, during storage, in the index ratchet embodiment.

Optimally, one of the radial compartments holds stop rings for the reamers; the compartment a perforated bottom to simplify picking up the rings with a reamer.

The invention also provides a dental tool kit comprising such a dental tool container having at least three different tools loaded in the compartments thereof.

Further objects of the present invention and its features will suggest themselves to those skilled in the art upon a reading of the present specification, together with the drawings annexed hereto wherein, throughout the several views, similar reference characters denote similar elements.

DETAILED DESCRIPTION OF THE INVENTION

Figure 1:
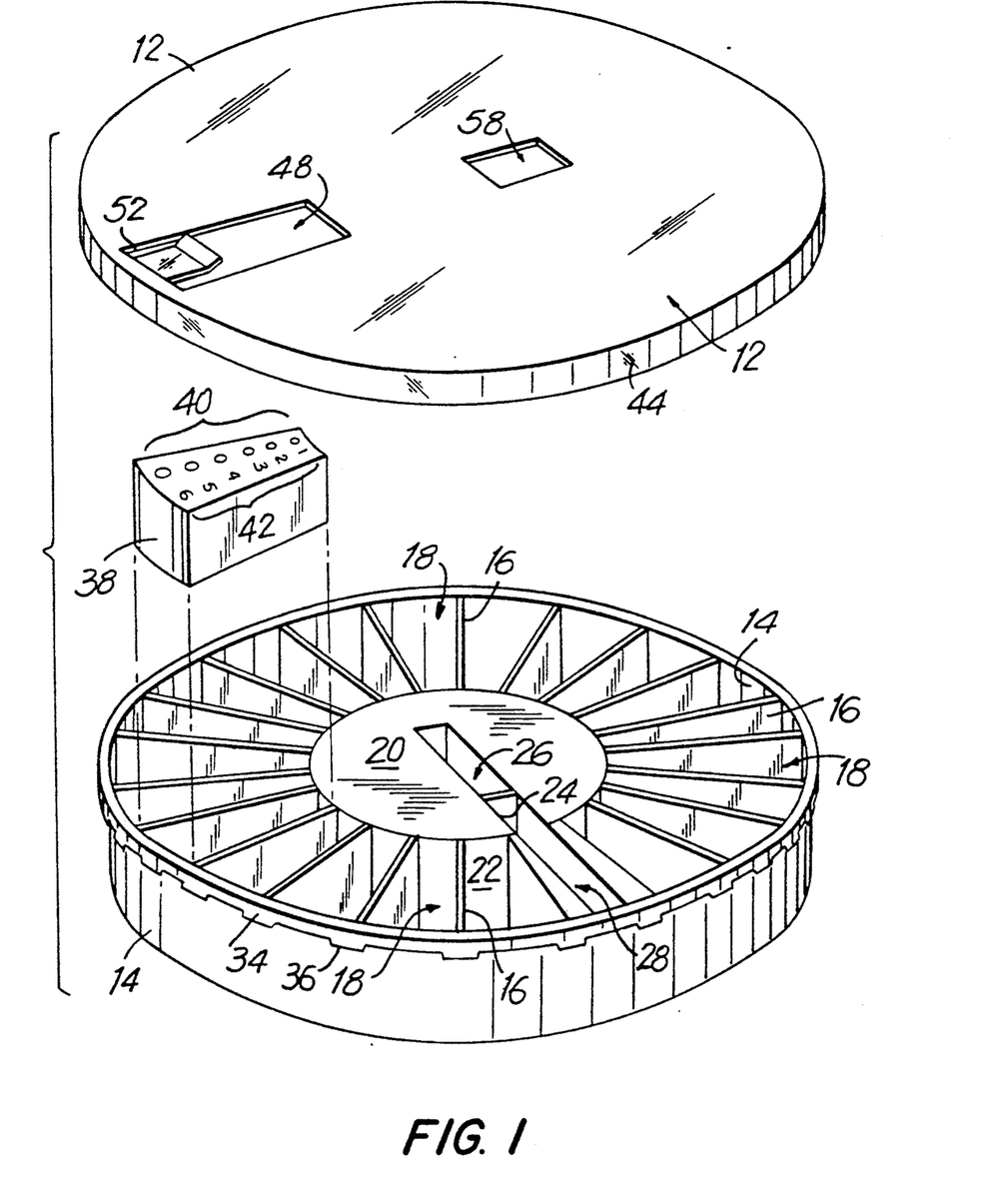
FIG. 1 is an exploded perspective view of one embodiment of a dental tool container according to this invention.
Figure 2:
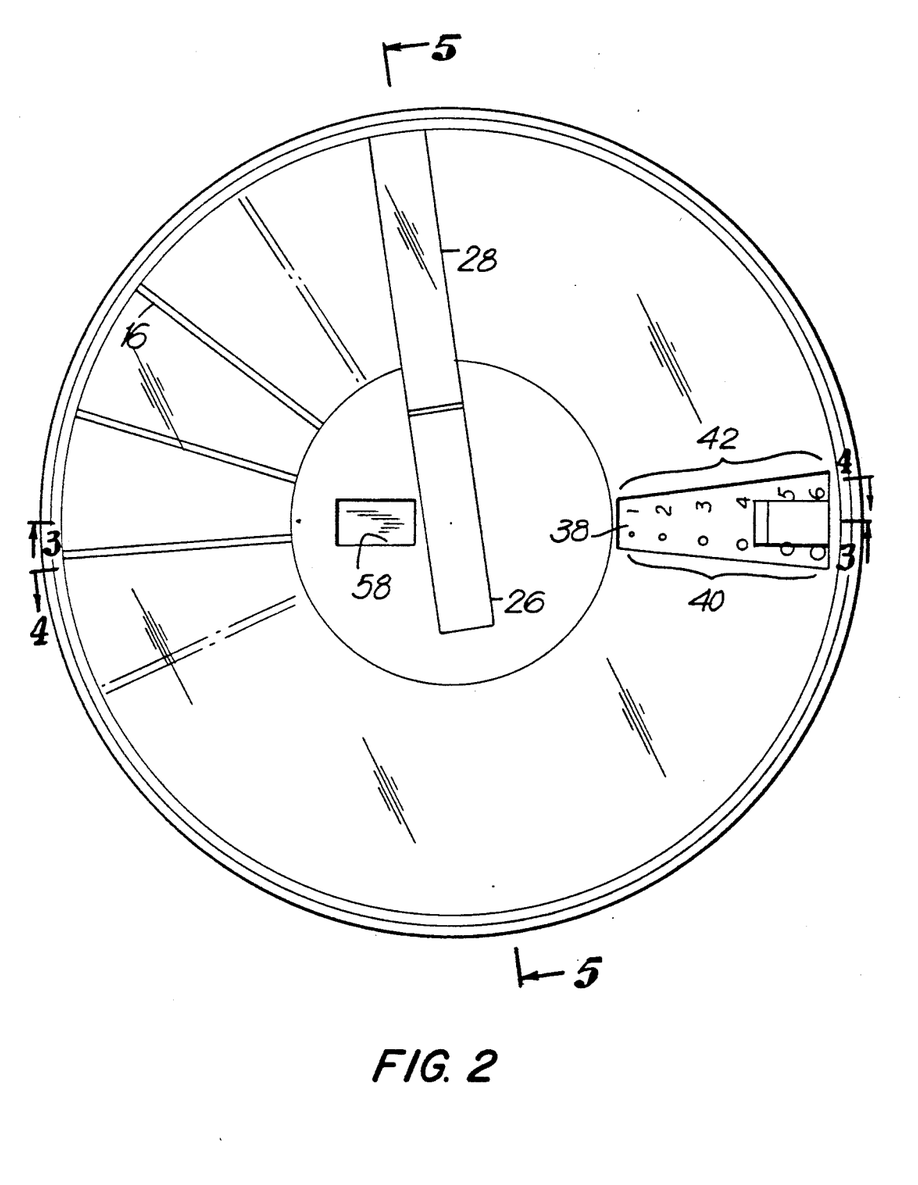
FIG. 2 is a top plan view of the dental tool container of FIG. 1 with a lid rotated to a different position from that shown in FIG. 1.

Referring to FIGS. 1 through 6 of the drawings, the dental tool container shown comprises an annular or cylindrical tool holder 10 of circular shape in plan, and a generally circular selector lid 12. Directions such as "up" and "down" refer to the disposition of the dental tool container as shown in FIG. 1.

The tool holder 10 is in the nature of a small circular tray and has a circular outer wall 14 from which radiate inwardly, at regular intervals, a number of dividing walls 16. The radial dividing walls 16 define primary tool-storage compartments 18 suitable for storing drill posts, or the like, for use with dental drills. The primary compartments 18 are truncated wedge-shaped and arranged in an annulus around the tool holder 10 with their inner walls 22 defining an inner circumferential skirt of a central circular platform 20; the platform top surface can be coplanar with the top edges of the dividing walls 16, or it can be elevated slightly above the walls 16, as explained below.

Clearly, the number of primary compartments 18 can be varied within the spirit of this invention, but a substantial number, for example from 10 to 30, is useful, and this first preferred embodiment shown has 21.

Cutting across this structure is a radial slot divided by a transverse wall 24 into a centrally disposed secondary tool storage compartment 26 and an outwardly extending, deeper, reamer compartment 28. The secondary compartment 26 and the reamer compartment 28 are both approximately rectangular in all sections. In the preferred embodiment shown, the reamer compartment 28 has the same depth as the primary compartments 18 and shares a circular annular floor 30 with them. The reamer compartment 28 extends radially inwardly somewhat beyond the primary compartments 18, to accommodate reamers which are usually longer than drill posts.

As may be seen by a careful reading of the drawings, the tool holder 10 is formed in a continuous skin 32 around the secondary compartment 26 which skin merges into the platform 20 so that the underside of the tool holder 10 is closed off.

The upper edge of the outer wall 14 carries an outwardly extending cover-bearing lip 34 around its periphery from which depend a series of small retainer teeth 36 spaced apart at regular, close intervals around the lip 34. Alternatively, the lid can be primarily supported by the inner wall 22, if it extends above the level of the divided walls 16 and the outer wall 14.

A solid gauge block 38 is located in one of the primary compartments 18 and is shaped to be a close, friction fit therein so as to be supported in its compartment 18 in a stable, immobile manner. The gauge block 38 is preferably formed of a hard, machinable material, for example, a metal such as aluminum or an aluminum alloy. A line of graduated gauge holes 40 labelled at 42, is provided along the upper face of the gauge block 38.

The selector lid 12 is also circular, to fit over the tool holder 10, and has a downward peripheral rim 44 terminating in a retainer flange 46, extending under the retainer lip 34 on the tool holder 10 on which the lid 12 is a, preferably close, rotatable fit.

A tapered primary opening 48 extends radially inwardly from the outer edge of the selector lid 12 and is positioned and shaped to provide access to the primary compartments 18. The plan shape of the primary opening 48 matches the wedge shape of the primary compartments 18, so that the gauge block 38 can be removed therefrom, if desired.

In a preferred embodiment, the dental tool container 10 is supplied to a dentist with a breakaway tab 50 attached to the outer edge 52 of the primary opening 48. On its underside, the tab 50 can have a pointed wedge 54 (FIG. 3) which fits into one of the gauge holes 40 in the gauge block 38, the tab 50 being downwardly biased so that the selector lid 12 is locked against rotation. The breakaway tab 50 can be an integral plastic molding with the selector lid 12, with score lines 56 providing a weakened seam along which the tab 50 can be removed from the lid 12 by tearing it off.

Aligned with the primary opening 48, on a common diameter of the selector lid 12 and across the center of the lid 12 so that it is radially offset therefrom, is a rectangular secondary opening 58 which can be rotated with the lid 12 into a position which provides access to the secondary compartment 26 simultaneously with access to the reamer compartment 28.

The dental tool container of this invention is designed to be economically and easily fabricated, for example by injection molding from a plastic such as polypropylene, or polycarbonate, and the lid 12 is preferably transparent or translucent to reveal the contents of the tool holder 10. A temperature-resistant plastic, for example polycarbonate, is desirable if sterilization of the container is required.

The platform 20 provides a convenient surface for an identification or informational label or legend.

Figure 3:
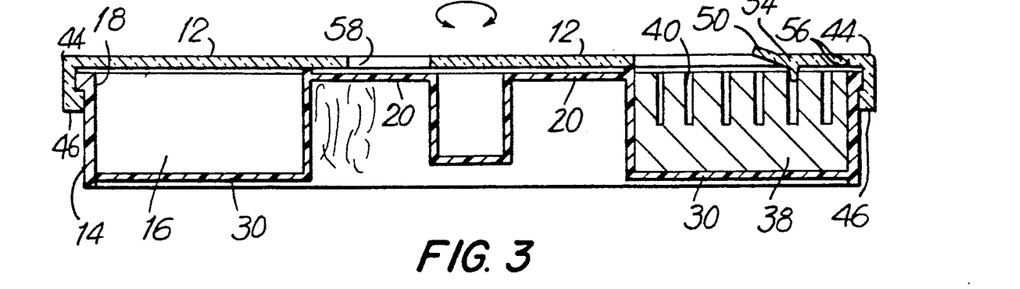
FIG. 3 is a section on the line 3—3 of FIG. 2 with the lid in the position shown in FIG. 1.

The dental tool container shown in the drawings can be distributed and sold with the breakaway tab 50 in the position shown in FIGS. 1 and 3 with the pointed pin on the underside of the tab 50 pressed into one of the gauge holes 40 in the gauge block 38, so that the tab 50 restrains the selector lid 12 from rotating. In this position, the breakaway tab 50 locks the lid 12 against rotation, while at the same time retaining the gauge block 38 in its compartment 18.

Preferably, the gauge block 38 is located in a primary compartment 18 which is displaced from the reamer compartment 28 by from sixty to one hundred and twenty degrees, for example, by approximately ninety degrees, or a little more. This displacement serves to position the secondary opening 58 over the central platform closing the secondary compartment 26. All the compartments, the primary compartments 18, the secondary compartment 26 and the reamer compartment 28, are thus closed.

The dental tool container can thus be shipped and supplied with the primary compartments 18 charged with dental posts or other tools, with one or more post wrenches in the secondary compartment 26 and with the reamer compartment 28 stocked with reamers, all these tools being secured in their respective compartments by the selector lid 12. It is a valuable feature of this invention that the three different types of compartment can be securely closed for distribution, without the need for a second lid or cover, yet be readily accessible to the user after sale.

A dentist, or other technician, tears off the breakaway tab 50 to release the selector lid 12. The selector lid 12 can then be rotated on the tool holder 10, riding on the cover-bearing lip 34 (or the inner wall) and being retained thereon by engagement of the retainer ring 46 on the lid 12 with the retainer teeth 36 depending from the lip 34 on the tool holder 10.

Rotation of the selector lid 12 sequentially registers the primary opening 48 with each primary compartment 18 in turn, so that the dentist or technician can remove a tool, such as a dental post, from a selected compartment 18, or replace it therein.

The reamer compartment 28 is also accessed through the primary opening 48. Although reamers may be longer than the opening 48, they can readily be lifted out through it. Alternatively, the opening 48 could be extended inwardly to be as long as the reamer compartment 28. The reamer compartment 28 is easily identified, even by a busy dentist, by its central, or inward, protrusion beyond the primary compartments 18. With reamer in hand, the dentist can readily check its size by rotating the selector lid 18 to register the opening 48 with the gauge block 38, and inserting the reamer in one or more of the index holes 40.

Alternatively, with dental post in hand, a dentist can readily remove a post wrench from the compartment 26 by rotating the selector lid until the secondary opening 58 registers with the secondary compartment 26. The secondary compartment 26, which will probably be the most frequently used compartment if it contains wrenches, is readily identified and located because of its prominent position in the center of the dental tool container.

For storage, the selector lid 12 can be rotated until the primary opening 48 registers with the gauge block 38 so as to keep maintain the other compartments covered, to reduce the likelihood of contaminating the tools, noting that the secondary opening is closed by the platform 20 in this position.

The invention thus provides a convenient, compact multi-purpose dental tool container which is suitable for storing four different types of tool (including the gauge block 38) that are used cooperatively. The invention further provides a useful dental tool kit comprising the dental tool container together with the posts, wrenches, reamers and gauge block loaded as described, which kit makes these cooperatively used tools available to the dentist in a novel and helpful manner.

Figure 6:
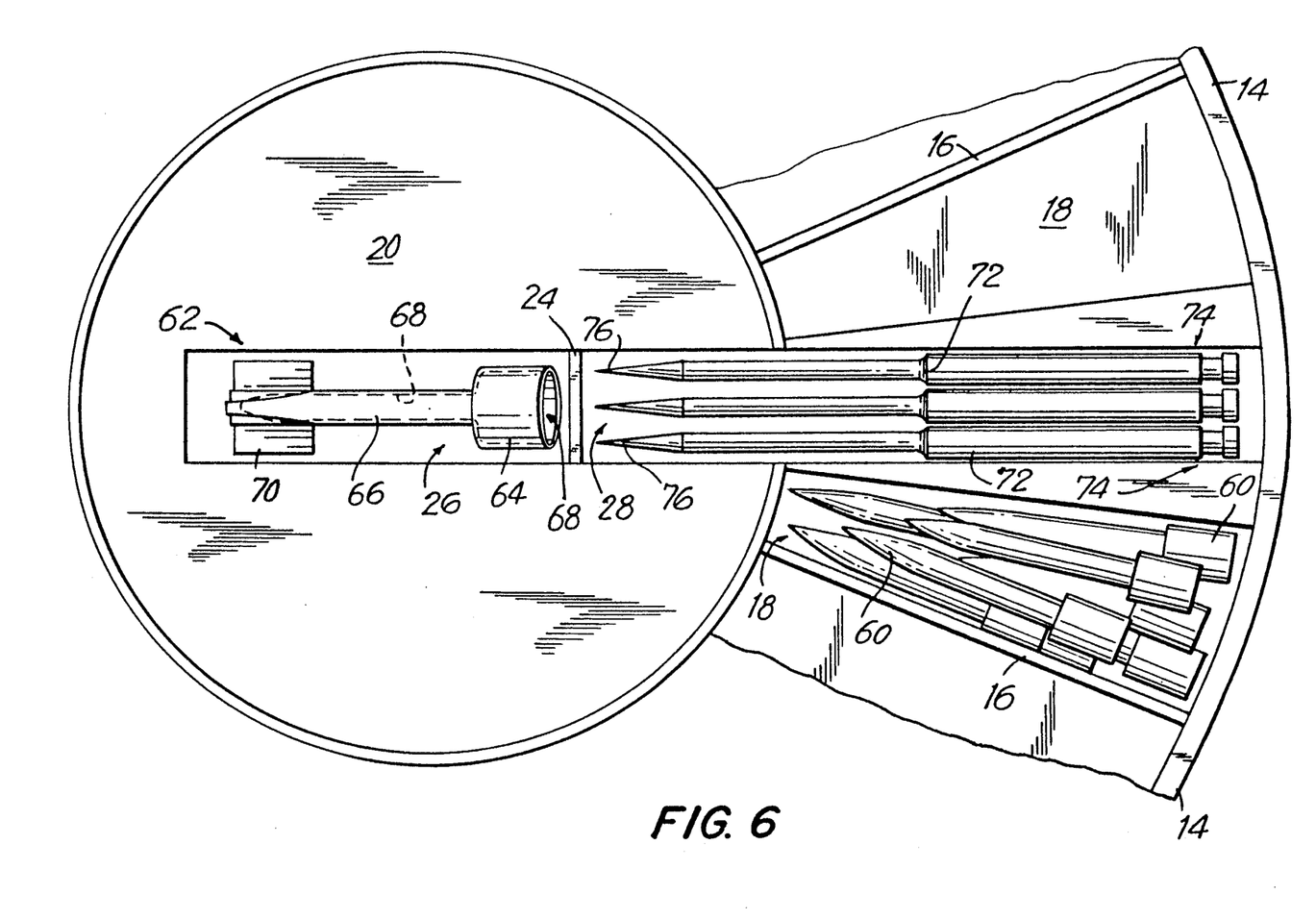
FIG. 6 is a partial, enlarged plan view of the dental tool container of FIG. 1, with the lid removed and with a number of internal compartments charged with a variety of dental tools.

FIG. 6 shows one way in which a variety of dental tools might be packed or loaded into the tool holder described above, to provide such a simple, compact dental tool kit. A number of dental posts 60, perhaps five to ten with six depicted, is shown loaded into one of the primary tool-storage compartments 18. Other compartments 18 can be similarly filled or charged. The dental posts are depicted as torpedo-shaped with a generally rounded or circular cross-section.

At least two dental post wrenches 62, depending upon their size, can be accommodated in the secondary compartment 26. These wrenches 62 comprise a hollow drum 64 at one end of the wrench, defining a socket designed and sized to mate with the head of a dental post 60; the cavity 68 is a close fit to a dental post 60, so as to be able to grip it. The other end of the post wrench 62 has outwardly extending fins 70, preferably three, to enable it to be turned manually. Two or more post wrenches 62 can be stowed end-for-end in the secondary compartment 26, the socket end of one wrench nesting between the fins 70 of another; which effect is enhanced for post wrenches 62 having three fins 70.

Figure 4:
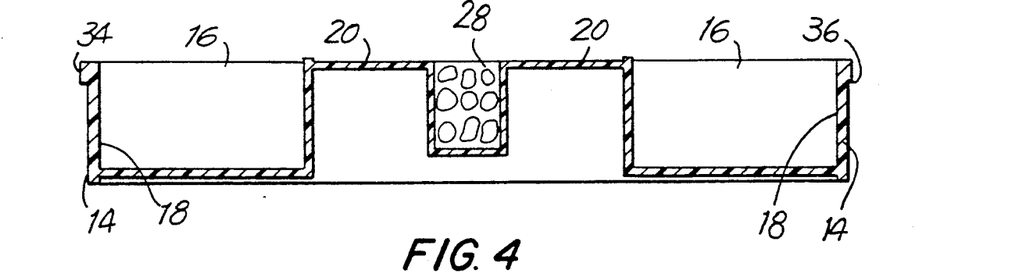
FIG. 4 is a section on the line 4—4 of FIG. 2 with the lid in the position shown in FIG. 1.
Figure 5:
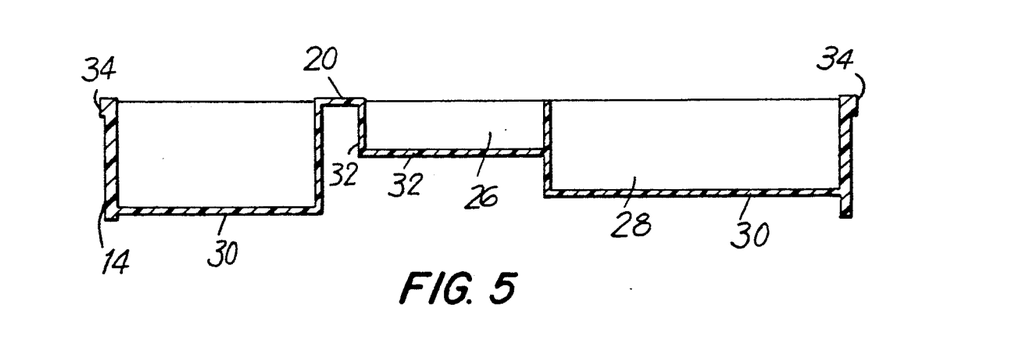
FIG. 5 is a section on the line 5—5 of FIG. 2 with the lid in the position shown in FIG. 1.

FIG. 6 read with FIG. 4 shows that, for example, up to nine reamers 72 can be stowed in the reamer compartment 28 and, noting that the attached figures are drawn approximately in proportion, the reamers 72 are too long to fit in either a primary compartment 18 or a secondary compartment 26. The reamers 72 are elongated, having a holder portion at one end for attachment to a dental drill handpiece, and a tapered operating end point 76, at the second end. A useful feature of this invention is that by providing for the primary opening 48, which is used to access the reamer compartment 28, to be shorter than a typical reamer 72, the reamers 72 can naturally be stowed with all their points 76 inwards, beneath the lid 12, reducing the chance of a dentist or technician pricking their finger while extracting a reamer 72 from the dental tool container. Such minor wounds are greatly to be avoided in the dental environment as they offer a potentially dangerous route of infection.

The construction of a dental tool kit comprising the container and tools as described and shown, is compact and economical without sacrificing utility, and the container is uniquely designed to satisfy the requirements of both distribution and use with a minimum of parts.

Other embodiments of the dental tool container and kit in accordance with the present invention are shown by FIGS. 7 through 18. As shown by these drawings, there are several primary modifications to the first embodiment, and several alternative minor changes within the changed broader concept. In accordance with the primary changes in concept embodied in the second group of embodiments, there are two elongated substantially rectangular compartments generally shown as 128 and 139, extending from the outer wall 114 of the container 110 through and beyond the inner circumferential wall 122, i.e., each extending almost to the center of the cylindrical container 110. The internal width of these compartments is preferably no greater than the minimum width of the remaining wedge-shaped primary compartments, generally designated as 118.

Figure 7:
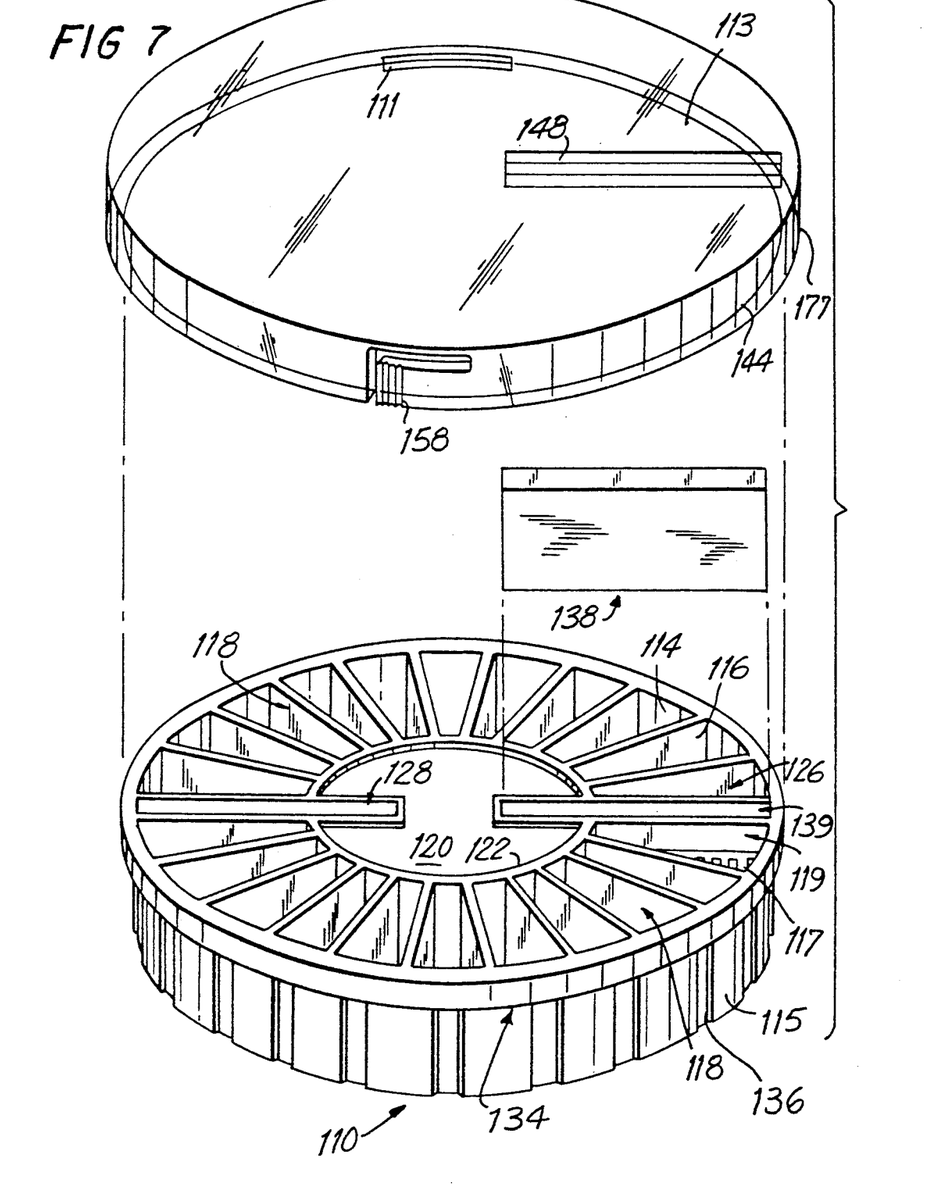
FIG. 7 is an exploded perspective view of a second embodiment of a dental tool container according to this invention.
Figure 7A:
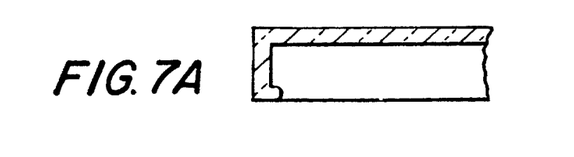

The central portion 120, within the inner circumferential wall 122, is otherwise covered by a plate 120, upon which can be secured a label or other material imprinted directly onto the wall surface 120.

One of the elongated rectangular chambers 128 is designed to hold the relatively longer reamer tools, and is thus designated the reamer compartment 128. The second elongated rectangular compartment 139, is designed to hold the gauge block 136. The remaining twenty-two (22) primary storage compartments 118 are each separated by relatively thin side walls 116, which extend substantially along radii of the cylindrical container between the outer circumferential wall 115d and the inner circumferential wall 122. These primary compartments, each generally indicated by the numeral 118, are thus each substantially segments of a cylinder. At least one of these primary compartments 118 is identified as a stop holder compartment 119, and is provided with perforated platform 117. The purpose of the platform is explained below.

An outwardly extending flange 134 is formed on the upper portion of the outer circumferential wall 114. Indexing grooves 136 extend longitudinally along the outer circumferential wall, from the flange 134 to the bottom of the container 10.

Figure 8:
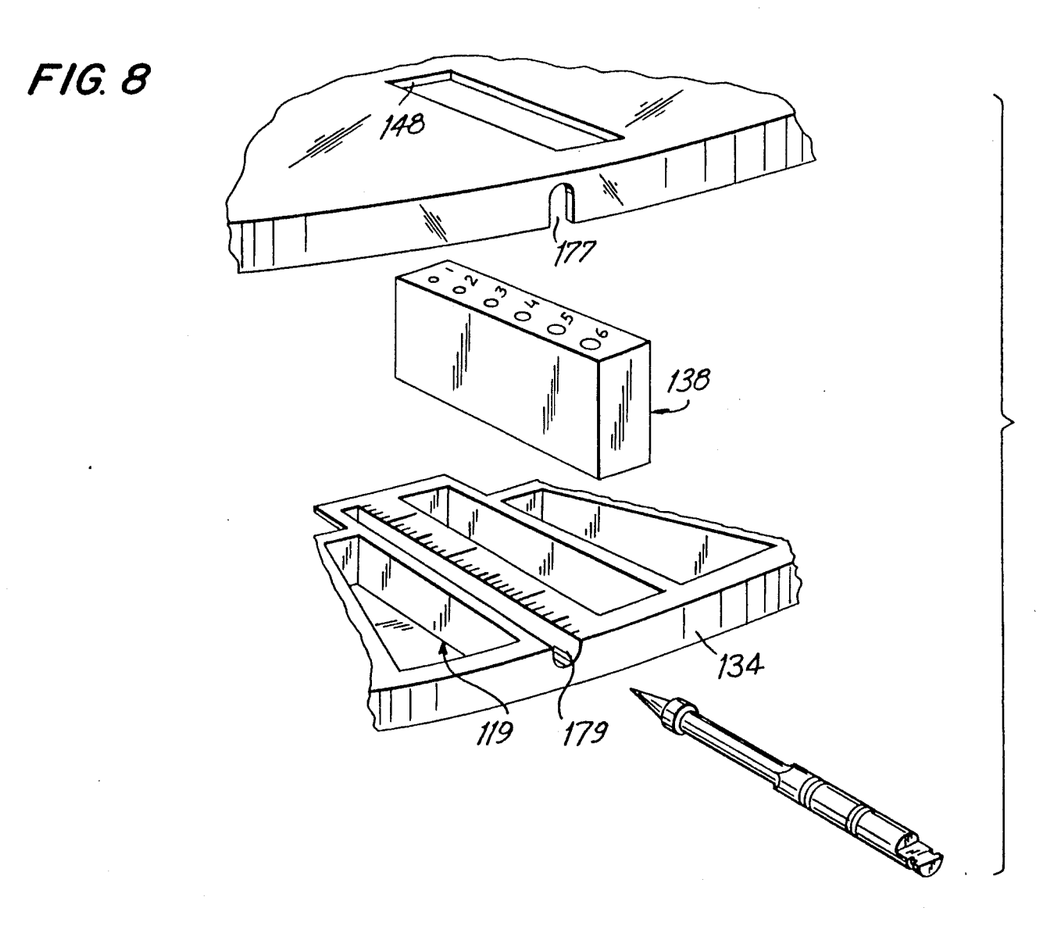
FIG. 8 is an exploded partial perspective view of the second embodiment of FIG. 7 showing the measuring scales according to this invention.

A substantially radially extending measuring groove 179 is formed along the top surface of the compartment wall separating the gauge block compartment 139 from the adjacent stops compartment 119. This measuring groove 179 extends from the upper lip 134 radially inwardly, alongside the gauge block compartment, generally measuring at least about thirty-five (35) millimeters in length.

The clear lid 112 for this container of the second embodiment is also formed of substantially transparent plastic and is generally cylindrical in shape, having a circular top 113 and a circumferential skirt 144, dependent from the top. The lid 112 has a single primary opening 148 in the shape substantially of a rectangle extending towards the center of the lid substantially from the outer rim 144. The opening 148 is so shaped as to be registrable with and to extend substantially the same length as the reamer compartment 128, but preferably should not extend up to the center of the lid. Preferably, the gauge block 138, and its block compartment 139, are not longer than the reamer tool compartment 128.

Figure 14:
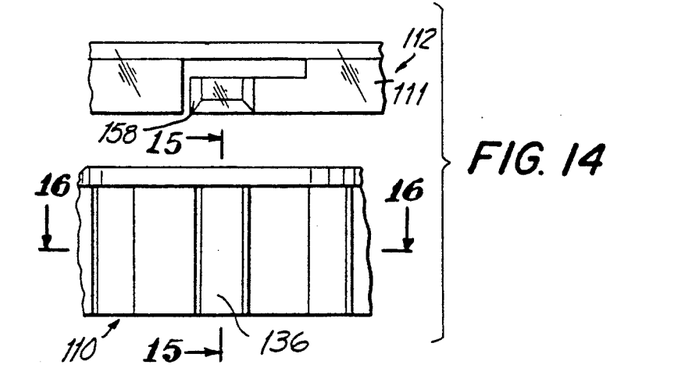
FIG. 14 is partial exploded side elevation view of the lid of FIG. 7, showing the index pawl.
Figure 15:
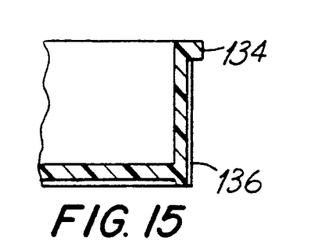
FIG. 15 is a section on the line 15—15 of FIG. 14.
Figure 16:
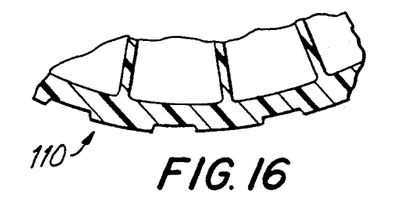
FIG. 16 is a section on the line 17—17 of FIG. 14.
Figure 17:
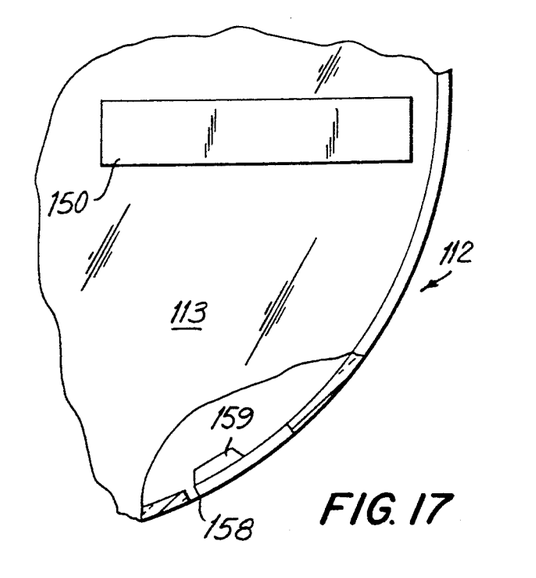
FIG. 17 is a partially sectioned partial top plan view of the container lid of FIG. 13.
Figure 18:
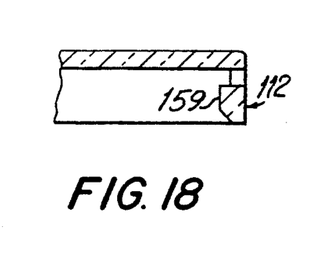
FIG. 18 is a radial elevation cross-section of the container lid of FIG. 7.

In this second preferred embodiment of the present invention, the removable locking pin and tab 50 are replaced by a permanent indexing ratchet system, comprising an indexing pawl 158 and the index slots 115. The indexing pawl 158 is flexibly connected to the lid side wall 111, but as is shown in the drawings, the indexing pawl 158 can be formed integral with the lid, but of a flexible material. The indexing pawl 158 is designed to fit within the indexing grooves or slots 136 along the outer surface of the container 110, and to fit under the flange 134, so as to engage the bottom surface of the flange 134 with the upper surface of the ratchet pawl 158. A partial reentrant lip 111 is secured to and extends inwardly from the inner surface of the lid skirt 144, at a location substantially 180° from the ratchet pawl 158. The reentrant lip 111 is located on the lid skirt 111 so as to fit under and to contact the bottom surface of, the container flange 134. The lid 112 is thus held in place on the container 110 by the interaction between the reentrant lip 111 on one side of the lid and the top surface 159 of the pawl 158 on the other side of the lid 112, and the bottom surface of the flange 134.

A concave side slot defined by curved surface 177 is located slightly offset from the access opening 148 in the lid and extends through the lid skirt 111. The side slot 177 and the tool opening 148 are so juxtaposed that when the opening 148 is registered above the gauge block 138, the lid slot 177 registers with the measuring groove 179 along the container top surface. Further, when the latter items are in register, one with the other, the indexing ratchet pawl 158 registers with one of the indexing ratchet slots 136.

In this second preferred embodiment, the container is originally supplied to a dentist with the tool opening 148 closed off by a breakaway covering sheet 150, secured to the lid. The covering sheet substantially prevents any of the tools stored in any of the compartments from falling out of the container, even if the container is overturned and regardless of the rotational position of the lid 112. It is thus not necessary to lock the lid in any particular rotational position. It has been found, that during actual use by a dentist, the indexing ratchet is sufficient to maintain a desired rotational position of a lid while removing a desired tool, or when not in use to retain the lid in the position where the opening 148 is registered over the measuring gauge block 138.

Although the measuring gauge compartment and the reamer compartment are shown 180° apart, these locations can be spaced more closely, as long as there is sufficient distance to avoid intersection of the two compartments. Thus, in most situations, these items can be anywhere from 60° to 180° displaced. Again, the measuring groove is shown immediately adjacent the gauge block compartment, thus permitting measuring both the diameter, or gauge, of the reamer and measuring the length of the reamer without moving the lid. By placing the stop compartment 119 immediately adjacent the gauge block, the rotation of the lid once the stop has been engaged on the reamer is reduced to a minimum. It is also, of course, possible to provide several such slots 177 around the circumference of the lid skirt 144. Preferably, the indexing pawl 158 is located about 60° of rotation away from the opening 148 and slot 177.

Figure 13A:
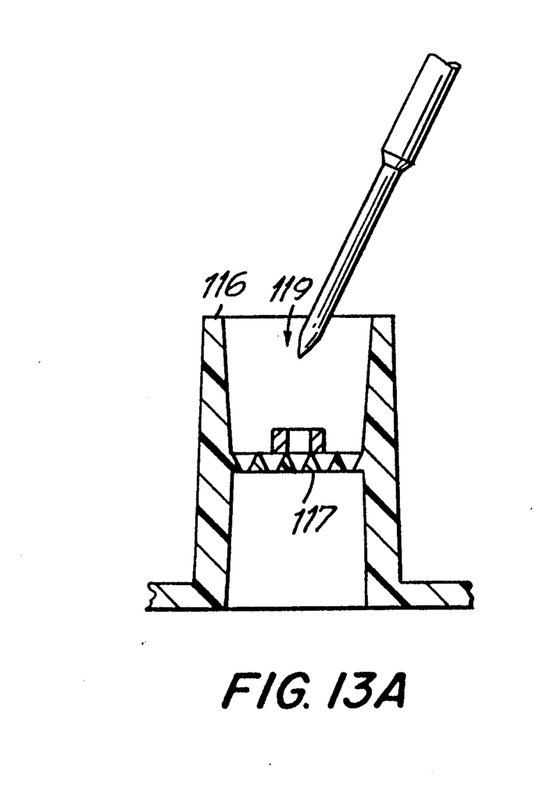
FIGS. 13a, b, c are a series of cross-sections of the stop compartment of FIG. 10, showing the application of a stop to a reamer.
Figure 13B:
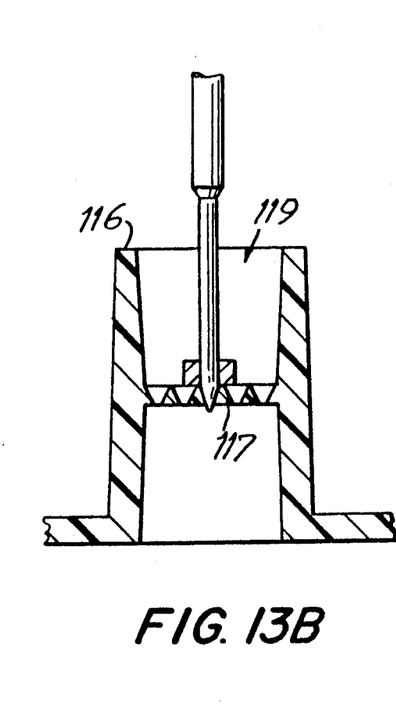
Figure 13C:
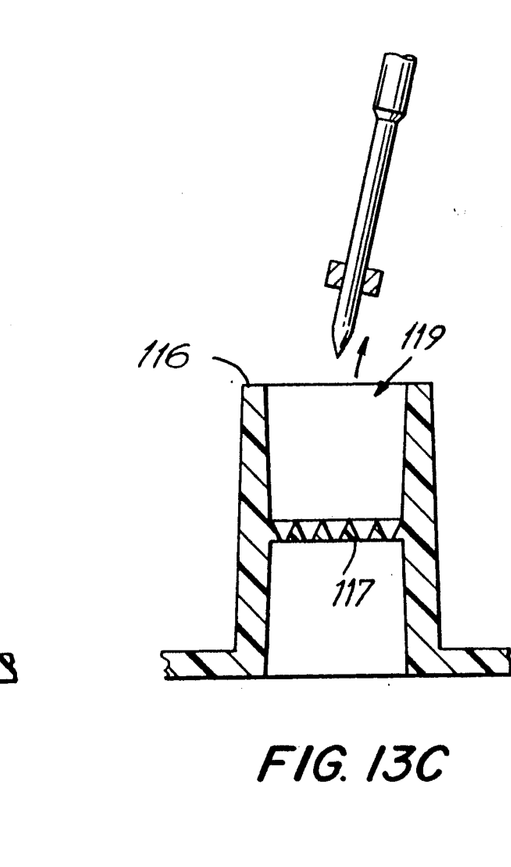

In use, the presence of the perforated platform 117 in the stop compartment 119 significantly eases placing, or impaling, the stop onto a reamer. The perforated platform 117, which can be wedged within the compartment, or can stand above a lower floor, permits the reamer to extend through the stop and into the floor, thus enabling the stop to be impaled and easily withdrawn from the compartment, as shown in FIGS. 13a–c. Thereafter, the stop can be moved to the desired position on the reamer by placing the tip of the reamer through the lid slot and pushing the reamer tip along the measuring groove 179, until the point of the reamer reaches the desired measured length, and the stop then provides the desired drill length for the particular use to which the dentist wishes to put the reamer. This series of actions are shown by FIGS. 14a, b and c and, for example, by FIG. 9.

Figure 9:
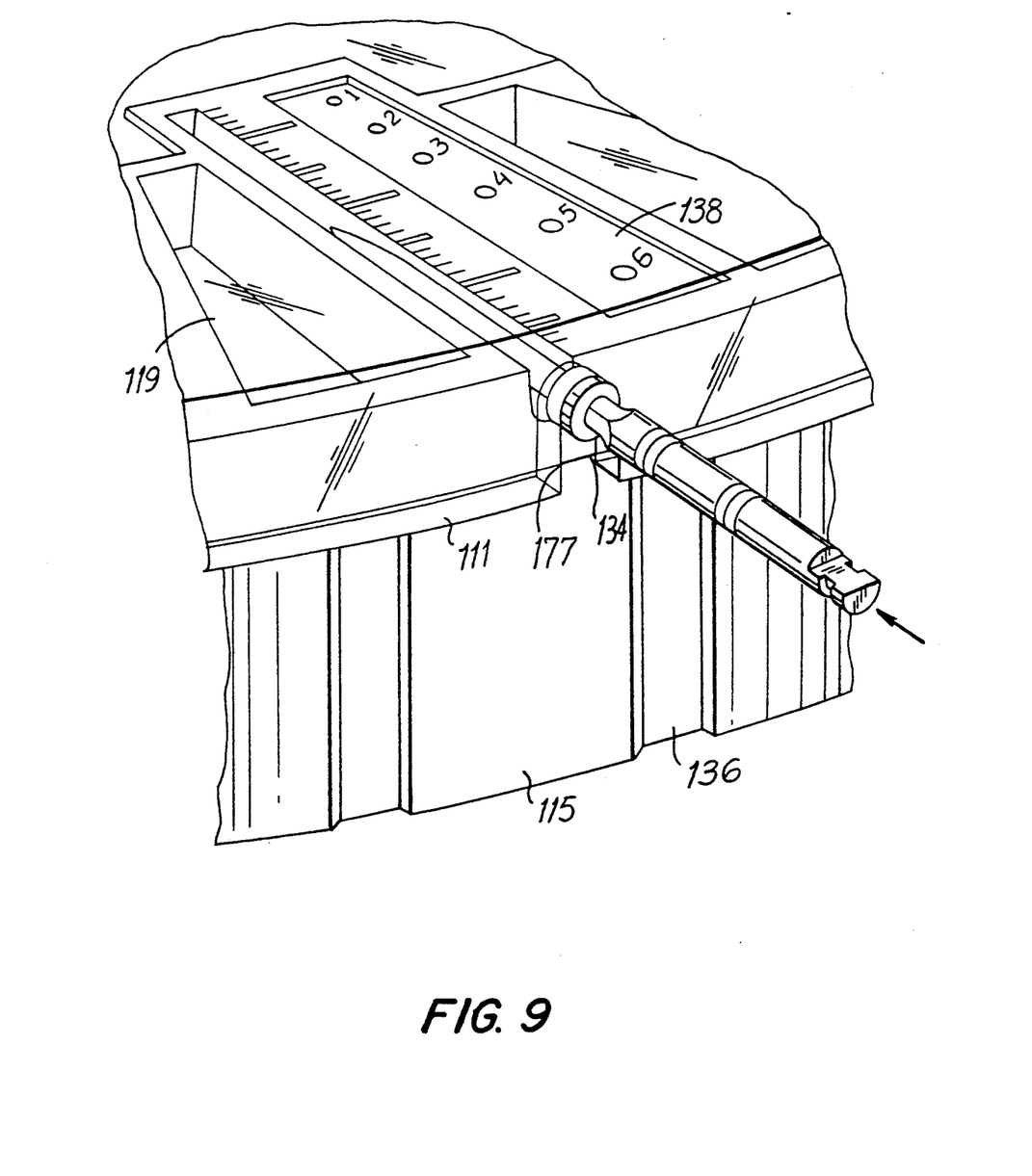
FIG. 9 is a partial perspective view of the second embodiment of FIG. 8, showing a reamer with a stop in place, showing a measuring scale on the container.
Figure 10:
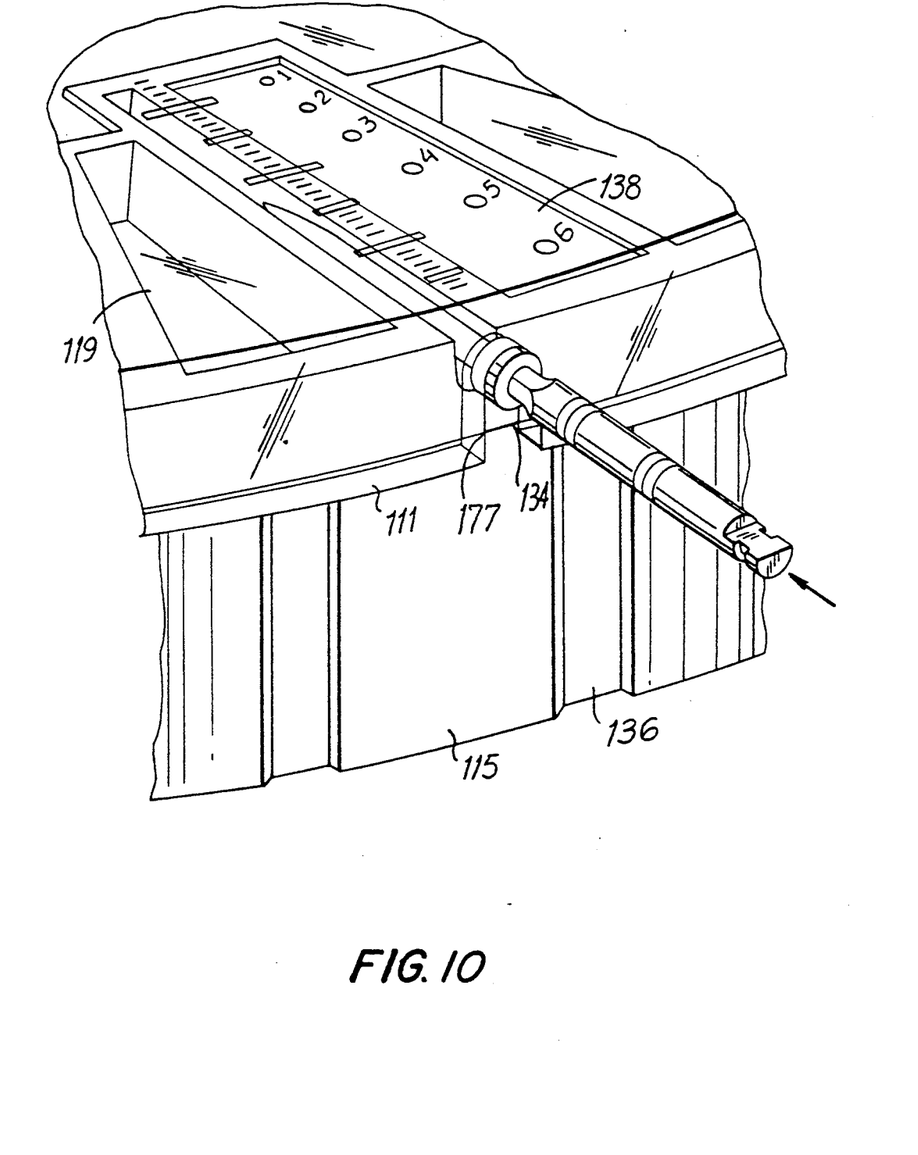
FIG. 10 is a partial perspective view of an alternative form of the second embodiment of FIG. 9, showing a measuring scale on the lid.

In FIG. 9, the longitudinal measuring gauge marks are formed on the top surface of the container, on the top surface of the wall separating the groove 179 from the gauge block compartment 139. In an alternative embodiment, the measuring marks can be formed on the lid top 113, as is shown in FIG. 10. In this case, the gauge marks are formed radially inwardly from the lid slot 177, such that when the lid slot is in registry with the measuring groove 179, the measuring marks extend across and above the measuring groove 179.

Figure 11:
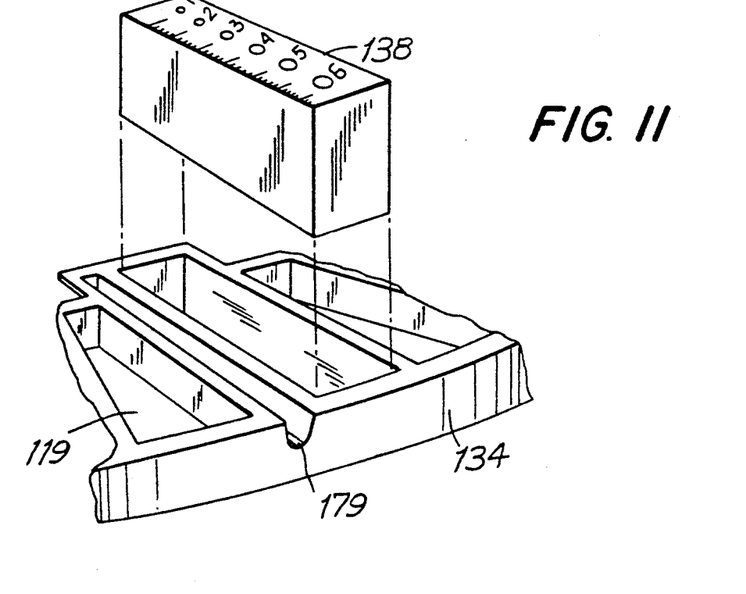
FIG. 11 is an exploded partial perspective view of an alternative form of the second embodiment of FIG. 9, showing a measuring scale on the gauge block.
Figure 12:
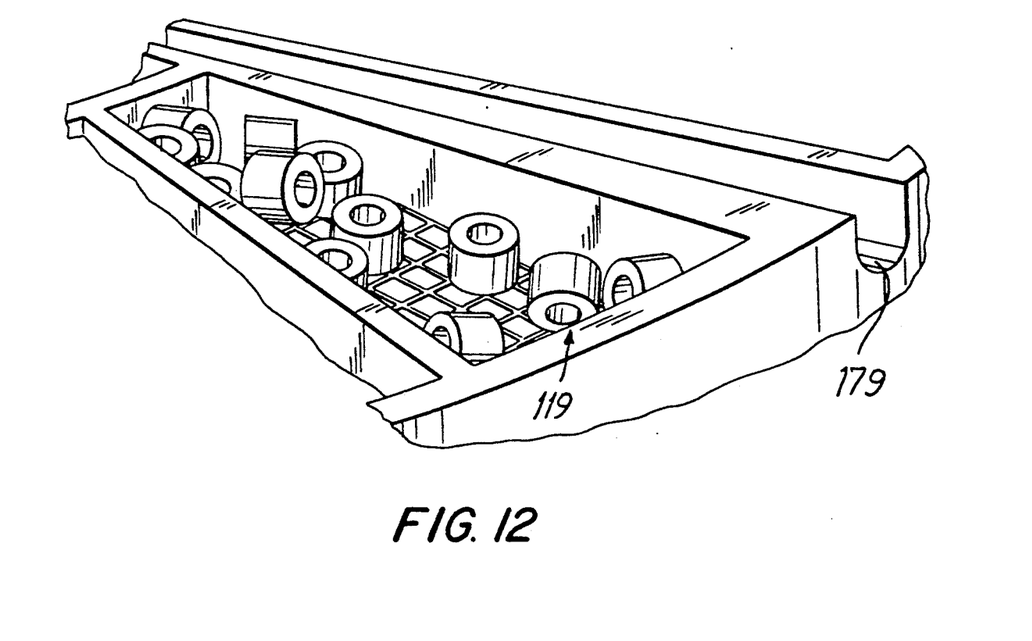
FIG. 12 is a partial perspective view of the second embodiment of FIG. 8, showing the stop compartment.

In yet another embodiment the measuring marks can be formed along the gauge block 138.

Preferably, the container has a substantially continuous bottom surface wall 130 forming a floor for all of the compartments.

The gauge block 138 is preferably a tight friction fit within the gauge block compartment 139, and can also be adherently cemented to the side walls and/or to the lower floor by known cement materials. The gauge block 138 can be formed from a rigid material such as a metal, e.g., aluminum or magnesium.

The container of this invention is not limited to any particular size or contents, and can be adapted for storing a variety of tools or other articles. However for the particular dentistry purposes described, the container is conveniently of a size to be held in the hand, for example from two to six inches across. A preferred embodiment for storing and dispensing the tools described is a little over three inches in diameter, across the selector lid 12, and has twenty-two (22) primary compartments 18 that are about three-quarters of an inch long, and a reamer compartment 26 that is a little over an inch long, with a depth of about three-eighths of an inch for the primary compartments 18. The perforated platform 117 in the stop compartment 119 can be press fit in place above the floor, or it can rest on legs, not shown, supported by the floor 130.

The embodiments of the invention disclosed and described in the present specification and drawings and claims are presented merely as examples of the invention. Other embodiments, forms and modifications thereof will suggest themselves from a reading thereof and are contemplated as coming within the scope of the present invention.

What I claim is:

1. A dental tool container comprising:
   an annular tool holder;
   a plurality of primary tool-storage compartments for dental posts which compartments are disposed around the tool holder; one of said primary compartments being elongated to project centrally inwards beyond others of said primary compartments, to provide a reamer compartment to accommodate reamers;
   a selector lid rotatably mounted on the tool holder and covering the compartments;
   a primary opening in the selector lid for accessing said primary compartments
   whereby rotation of the selector lid can register said primary opening with each primary compartment in turn, providing access thereto;
   and wherein the tool container further comprises: a secondary tool storage compartment for dental post wrenches which secondary compartment is disposed centrally of the tool holder and surrounded by said primary compartments; and a secondary opening in the selector lid for accessing said secondary compartment;
   whereby rotation of the selector lid on the tool holder can bring the secondary opening therein into and out of registration with said secondary compartment to access it.

2. A dental tool container according to claim 1, wherein the secondary compartment extends across the holder to abut the reamer compartment.

3. A dental tool container according to claim 1, wherein the tool holder is generally cylindrical with a circular-section outer wall and the primary tool-storage compartments are wedge-shaped.

4. A dental tool container according to claim 3, wherein the tool holder further comprises a floor extending continuously beneath the primary and secondary compartments and between said compartments.

5. A dental tool container according to claim 1, having a breakaway tab to lock the selector lid in a closed position for distribution.

6. A dental tool container according to claim 1, having a gauge block in one of the primary compartments which block is adapted for measuring tools to be stored in others of said compartments.

7. A dental tool container according to claim 6, having a breakaway tab to lock the selector lid in a closed position for distribution which breakaway tab is adapted to engage the gauge block thereby to lock the selector lid against rotation and to hold the gauge block in its primary compartment.

8. A dental tool kit comprising a dental tool container according to claim 1, and at least three different tools loaded in the compartments thereof.

9. A dental tool kit according to claim 8, wherein dental posts and a gauge block are stored in the tool holder's primary compartments, reamers are stored in an elongated reamer compartment and one or more post wrenches is stored in the secondary compartment.

10. A dental tool kit comprising dental posts and dental post wrenches loaded in a dental tool container which container comprises:
    an annular tool holder;
    a plurality of primary tool-storage compartments disposed around the tool holder and charged with dental posts;
    a selector lid rotatably mounted on the tool holder and covering the compartments;
    a primary opening in the selector lid for accessing said primary compartments;
    whereby rotation of the selector lid can register said primary opening with each primary compartment in turn, providing access thereto;
    and wherein the tool container further comprises:
    a secondary tool storage compartment charged with dental post wrenches which secondary compartment is disposed centrally of the tool holder and surrounded by said primary compartments; and a secondary opening in the selector lid for accessing said secondary compartment;

whereby rotation of the selector lid on the tool holder can bring the secondary opening therein into and out of registration with said secondary compartment to access it.

11. In a dental tool container comprising:
   an annular tool holder having an outer circumferential wall and an inner circumferential wall;
   a plurality of primary tool-storage compartments for dental posts which compartments are disposed circumferentially around the tool holder;
   a solid surface extending across and sealing off one longitudinal end of each compartment;
   a selector lid rotatably mounted on the tool holder and covering the compartments; and
   a primary opening through the selector lid for accessing said primary compartments;

whereby rotation of the selector lid can register said primary opening with each primary compartment in turn, providing access thereto;

the improvement which further comprises:
      a perforated platform located within and extending fully across one of such primary tool storage compartments for the storage of dental reamer stops, the openings through the platform being of a size small enough to prevent passage of a stop but sufficiently large to accept at least the end point portion of a reamer; and a gauge block held within one of said primary compartments designed to measure the gauge of tools to be stored in the other compartments; and wherein one of said primary compartments is elongated to project centrally inwards through and beyond the inner circumferential wall to provide a reamer compartment to accommodate reamers;

whereby rotation of the selector lid on the tool holder can bring the primary opening therein into and out of registration with any of said primary compartments to access a tool, or with the gauge block to measure the diameter of a tool.

12. A dental tool container according to claim 11, wherein the elongated primary compartment has substantially parallel sides.

13. A dental tool container according to claim 12, wherein a second primary compartment is elongated to project centrally inwards through and beyond the inner circumferential wall, and wherein the gauge block fits snugly within this second elongated primary compartment.

14. A dental tool container according to claim 12, wherein the tool holder is generally cylindrical with a circular-section outer wall and at least a majority of the primary tool-storage compartments are truncated wedge-shaped in plan section.

15. A dental tool container according to claim 11, comprising a thickened divider wall between the gauge block compartment and the adjoining primary compartment, the divider wall having a top surface, a measuring groove formed into and along the top surface, extending inwardly from and through the outer circumferential wall, and measuring mark means for measuring the length of a tool resting within the measuring groove.

16. A dental tool container according to claim 11, wherein the lid comprises a top surface, through which the primary opening extends, and a circumferential skirt portion extending transverse to the top surface and surrounding at least a portion of the outer wall of the tool holder, at least one tool slot being formed through the skirt designed to permit the passage of a tool into the measuring groove when the lid is positioned such that the tool slot is in register with the measuring groove.

17. A dental tool container according to claim 16, further comprising indexing means secured between the lid and the container and designed to provide that any stable relationship between the angular position of the container and the lid places the primary opening in registry with a primary compartment.

18. A dental tool container according to claim 17, wherein the indexing means comprises a pawl flexibly secured to the lid and index slots formed along the outer circumferential wall of the container.

19. A dental tool container according to claim 11 having a breakaway tab to seal the primary opening in the lid.

20. A dental tool kit comprising a dental tool container according to claim 11 and at least three different tools, stop rings and a gauge block loaded in the compartments thereof.

21. A dental tool kit comprising dental posts, dental post wrenches, and dental reamers and dental reamer stops loaded in a dental tool container which container comprises:
   an annular tool holder;
   a plurality of primary tool-storage compartments disposed around the tool holder and charged with said dental tools;
   a selector lid rotatably mounted on the tool holder and covering the compartments;
   a primary opening in the selector lid for accessing said primary compartments;

whereby rotation of the selector lid can register said primary opening with each primary compartment in turn, providing access thereto;

and wherein the tool container further comprises:
      gauge block held within one of said primary compartments; and
      a perforated platform located within and extending across a second of said primary compartments, the dental reamer stops being charged to said second primary compartment.

22. A dental tool container comprising:
   an annular tool holder;
   a plurality of primary tool-storage compartments for dental posts which compartments are disposed around the tool holder; a perforated platform located within and extending fully across one of said primary tool-storage compartments for the storage of dental reamer stops, the openings through the platform being of a size small enough to prevent passage of a reamer stop but sufficiently large to accept at least the end point portion of a reamer;
   a selector lid rotatably mounted on the tool holder and covering the compartments; the perforated platform extending along a plane sufficiently distant from the selector lid to permit the placement of reamer stops in the compartment without interfering with the rotation of the lid;
   a primary opening in the selector lid for accessing said primary compartments;

whereby rotation of the selector lid can register said primary opening with each primary compartment in turn, providing access thereto.

23. The dental tool container of claim 22, wherein the tool container further comprises:

a secondary tool storage compartment for dental post wrenches, which secondary compartment is disposed centrally of the tool holder and surrounded by said primary compartments; and a secondary opening in the selector lid for accessing said secondary compartment;

whereby rotation of the selector lid on the tool holder can bring the secondary opening therein into and out of registration with said secondary compartment to access it.

* * * * *